United States Patent
Liang

(10) Patent No.: US 8,926,621 B2
(45) Date of Patent: Jan. 6, 2015

(54) SURGICAL INSTRUMENT FOR ACETABULAR CUP IMPLANTATION

(71) Applicant: United Orthopedic Corporation, Hsinchu (TW)

(72) Inventor: Chih Ming Liang, Hsinchu (TW)

(73) Assignee: United Orthopedic Corporation, Hsinchu (TW)

( * ) Notice: Subject to any disclaimer, the term of this patent is extended or adjusted under 35 U.S.C. 154(b) by 196 days.

(21) Appl. No.: 13/718,647

(22) Filed: Dec. 18, 2012

(65) Prior Publication Data

US 2014/0081283 A1 Mar. 20, 2014

(30) Foreign Application Priority Data

Sep. 18, 2012 (TW) .............................. 101134201 A

(51) Int. Cl.
*A61B 17/88* (2006.01)
*A61F 2/46* (2006.01)
*A61F 2/30* (2006.01)

(52) U.S. Cl.
CPC ..... *A61F 2/4609* (2013.01); *A61F 2002/30471* (2013.01); *A61F 2002/4627* (2013.01); *A61F 2002/4628* (2013.01); *A61F 2002/4629* (2013.01)
USPC .............................. 606/91; 606/99; 623/22.12

(58) Field of Classification Search
USPC ....... 241/91–93; 606/86 R, 91, 99; 623/22.12
See application file for complete search history.

(56) References Cited

U.S. PATENT DOCUMENTS

| | | | | |
|---|---|---|---|---|
| 7,785,329 B2* | 8/2010 | Lechot et al. | ................. | 606/81 |
| 7,857,816 B2* | 12/2010 | Burgi | ................. | 606/91 |
| 8,142,439 B2* | 3/2012 | Parker | ................. | 606/91 |
| 2005/0038443 A1* | 2/2005 | Hedley et al. | ................. | 606/91 |
| 2007/0293869 A1* | 12/2007 | Conte et al. | ................. | 606/91 |
| 2013/0226186 A1* | 8/2013 | Burgi | ................. | 606/91 |

* cited by examiner

*Primary Examiner* — Nicholas Woodall
*Assistant Examiner* — Larry E Waggle, Jr.
(74) *Attorney, Agent, or Firm* — Tim Tingkang Xia, Esq.; Morris, Manning & Martin, LLP

(57) ABSTRACT

A surgical instrument for acetabular cup implantation includes an acetabular cup, a shell body and a drive shaft. The drive shaft includes a drive rod and a handle bar. The handle bar engages the pivot for angular displacement having forward position and backward position. In the forward position the drive rod rotates the acetabular cup forward, and in the backward position the drive rod shifts backward resulting in the acetabular cup engaged the extension portion. Accordingly, the operator rotates the handle bar to control the acetabular cup inserting into the position of acetabulum. The rotation of the handle bar results in the gripping or releasing of the acetabular cup or insert from the invention. Thus the invention provides a clear and ergonomic instrument for medical personnel concerning the operation of acetabular cup implantation.

9 Claims, 8 Drawing Sheets

SURGICAL INSTRUMENT FOR ACETABULAR CUP IMPLANTATION

CROSS-REFERENCE TO RELATED APPLICATION

This application claims priority from application No. 101134201, filed on Sep. 18, 2012 in the Taiwan Intellectual Property Office, the entire content of is hereby incorporated by reference.

BACKGROUND OF THE INVENTION

1. Field of the Invention

The present invention is related to a surgical instrument, and more particularly to an ergonomic and easy constructional surgical instrument for acetabular cup implantation.

2. Description of Related Art

The hip joint is the joint between the femur and acetabulum of the pelvis and combines with articular hyaline cartilage, synovial membrane and labrum to form a ball-like joint. It is a special type of ball and socket joint and its primary function is to support the weight of the body in both static (e.g. standing) and dynamic (e.g. walking or running) postures.

The normal hip functions as a "ball and socket" joint, allowing smooth range of motion in multiple planes in motion of human body. Any condition that affects either of these structures can lead to deterioration of the joint. This, in turn, can lead to deformity, pain, and loss of function. The most common condition affecting the hip in this way is osteoarthritis. Other conditions that may affect the hip adversely include inflammatory arthritis (rheumatoid arthritis, psoriatic arthritis, spondyloarthropathies, etc.), developmental dysplasia, childhood hip disorders (Legg-Calve-Perthes disease, slipped capital femoral epiphysis, etc.), trauma, neoplasms, and osteonecrosis. When the injury or disease occurs the damage component(s) can be rebuilt or replaced using appropriate orthopaedic implants. In the technique known as "Total hip replacement", this involves surgical operation to clean femur and acetabulum, and then replace with artificial point.

A total hip artificial joint is a key prosthesis in the replacement operation. It consist of femoral stem, acetabular system (acetabular cup & acetabular liner & bone screw), Bipolar system (bipolar cup & bipolar liner), and metal ball head. The total joint replacement can require an acetabular cup component providing a bearing or articulating surface for the acetabulum and a femoral component providing an articulating surface for the femoral head. The acetabular cup and femoral components can generally be positioned relative to various portions of the associated anatomy in a substantially fixed manner. A liner fits inside the socket and allows the hip to move smoothly. A metal or ceramic ball that will replace the round head (top) of thigh bone. A metal stem is attached to the thigh bone to make the joint more stable.

It is key issue for medical personnel to insert the acetabular cup into the acetabulum. Medical personnel operate with the holder of acetabular cup inserter, which positions the acetabular cup by using screws to fix and insert acetabular cup inserter into the position of hip tissue of pelvis. After finishing insertion, the acetabular cup inserter is screwed to release the acetabular cup inside. Nevertheless, the acetabular cup inserters used nowadays are too structural complexes to handles easily; it brings no ergonomic resulting in difficulties to operate inserters.

In order to solve the problem(s), the present invention introduces a surgical instrument for acetabular cup implantation.

SUMMARY OF THE INVENTION

The primary objective of the present invention is to provide a surgical instrument for acetabular cup implantation which is a handy implantation instrument for medical personnel to improve surgical operation for total hip replacement.

In order to accomplish the above objective, the surgical instrument for acetabular cup implantation in accordance with the present invention comprises:

an acetabular cup having a hole thereon;
a shell body having a handle and an extension portion, wherein the extension portion has an end to cap the acetabular cup; and
a drive shaft being partly assembled in the shell body, including:
  a drive rod having a connector near the end of the extension portion to engage with the hole and a pivot at the other distal end; and
  a handle bar connecting to the pivot in the drive rod;
wherein, the handle bar with shifting angles drives the pivot forward and backward, in the forward position the handle bar moves the drive rod forward and is able to rotate the acetabular cup via the drive rod, and in the backward position the handle bar shifts the drive rod resulting in the acetabular cup engaged the end of extension portion.

In a preferred embodiment, the extension portion has an end equipped with a load-bearing head for engaging the acetabular cup.

In still another embodiment, the connector uses screw thread secures the acetabular cup.

In a preferred embodiment, the hole has female thread defined on inner surface and the connector has pin thread defined on outer surface.

In still another embodiment, the shell at least has a bush for housing the drive rod.

In a preferred embodiment, wherein the drive rod comprises: a first drive rod having the connector; a second drive rod using a first universal joint to connect the first drive rod: a third drive rod using a second universal joint to connect the second drive rod: a fourth drive rod using a third universal joint to connect the third drive rod: and a fifth drive rod having one end using a fourth universal joint to connect the fourth drive rod and other distal end connecting the pivot.

In still another embodiment, the handle has an end connecting a head.

In a preferred embodiment, the head has a guide hole to house the handle bar.

In yet another embodiment, the handle has a gasket on one side, and the handle bar includes a cam sliding on the gasket.

The drive shaft in surgical instrument for acetabular cup implantation includes a handle bar and at least a drive rod. The drive rode has the connector near the end of the extension portion to engage through the hole and a pivot at the other distal end. The handle bar engages with the pivot for angular displacement having forward position and backward position. The handle bar shown in surgical instrument has first place where an operator moves the handle bar to the forward position. Next, the operator rotates the handle bar to adjust the acetabular cup in the proper angle. After the acetabular cup is in the proper angle, the handle bar has second place where an operator moves the handle bar to the backward position. Then, the acetabular cup is fixed and cannot rotate. The operator inserts the acetabular cup in the position of acetabulum. After moving handle bar to forward position again, the operator rotates it to release the acetabular cup. Thus, rotation of the handle bar results in the gripping or releasing of the acetabular cup or inserts it from surgical instrument.

Furthermore, the surgical instrument can be operated and rotated with only one hand holding the drive rod. The invention provides a handy implantation instrument for medical personnel to operate without difficulties. It promotes ergonomic operation concerning the total hip artificial joint. The invention of surgical instrument for acetabular cup implantation provides a clear and ergonomic instrument for medical personnel concerning the operation of acetabular cup implantation and making practical progress on the field.

DETAILED DESCRIPTION OF THE INVENTION

The following description is merely exemplary in nature and is in no way intended to limit the present teachings, applications, or uses. Those of skill in the art will recognize that the following description is merely illustrative of the principles of the invention, which may be applied in various ways to provide many different alternative embodiments.

Figure 1:
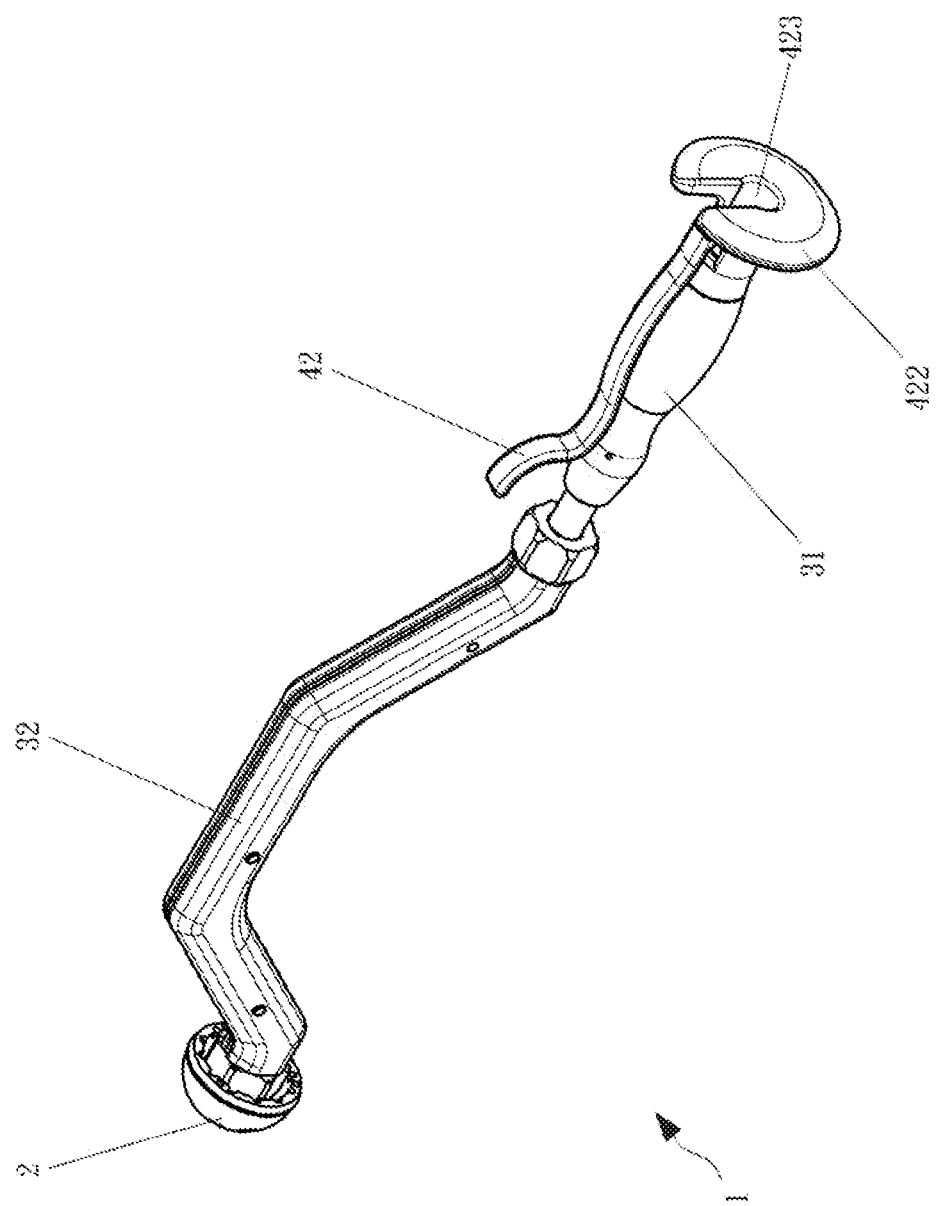
FIG. 1 is an isometric view of the preferred embodiment of the present invention.
Figure 2:
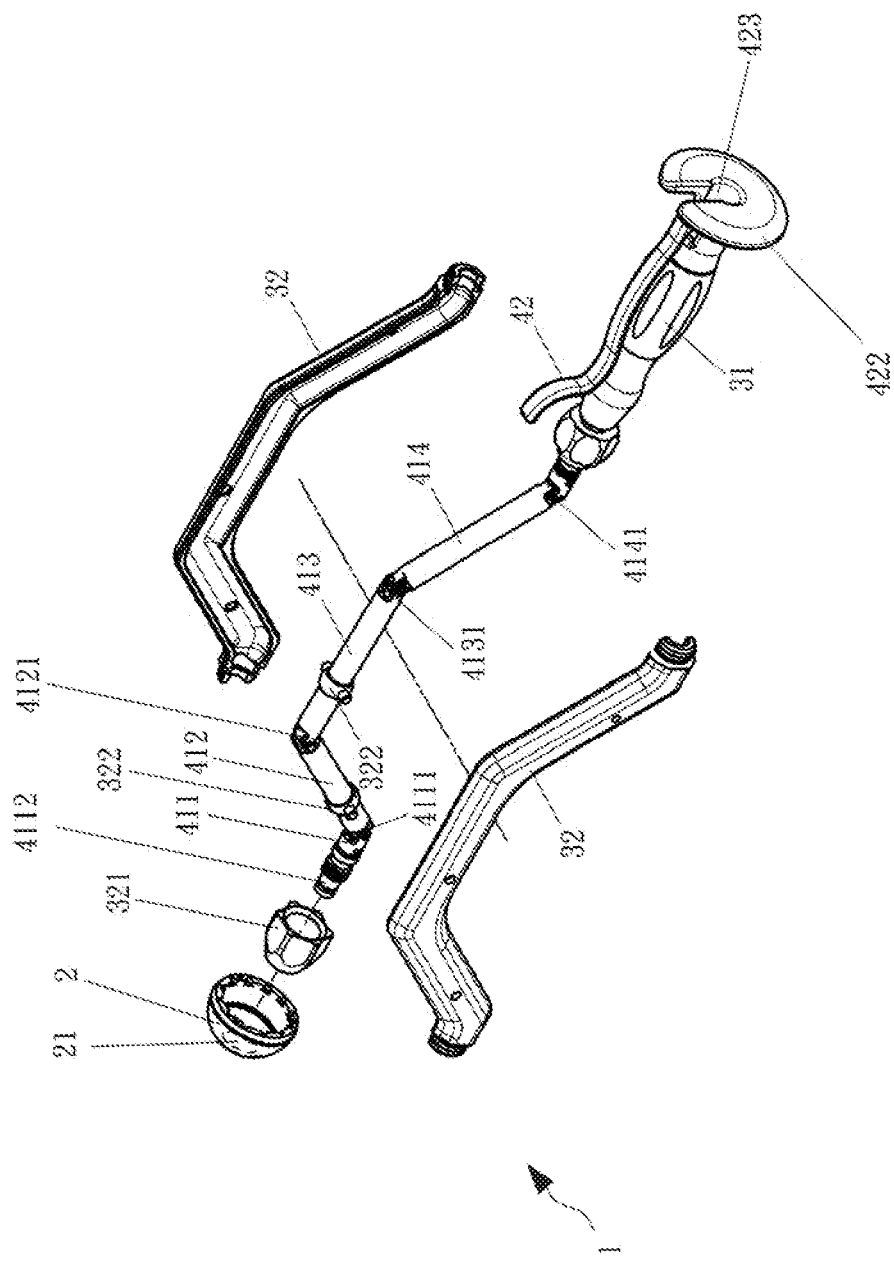
FIG. 2 is an assembled view of the preferred embodiment of the present invention.
Figure 3:
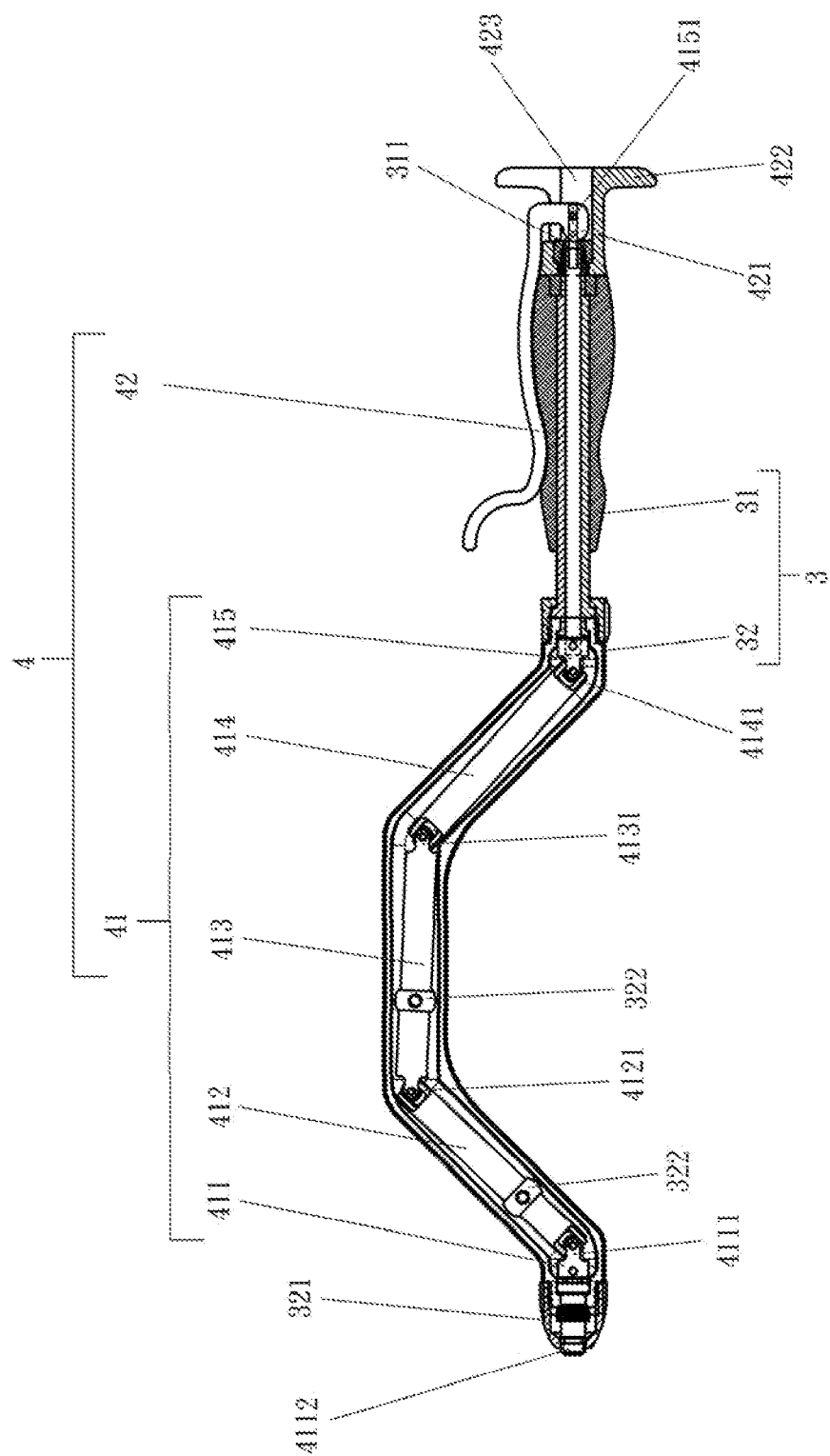
FIG. 3 is a cross-sectional of the preferred embodiment of the present invention.

With references to FIGS. 1, 2 and 3 are illustrations of the preferred embodiment of the present invention that the surgical instrument for acetabular cup implantation is illustrated in isometric view, assembled view and cross-sectional view separately. There is shown the surgical instrument 1 includes an acetabular cup 2, a shell body 3 and a drive shaft 4.

The acetabular cup 2 has a hole 21 thereon which is cut a female thread on the inner surface. In some embodiments, a plurality of holes may be preferred.

A shell body 3 has a handle 31 and an extension portion 32. The extension portion 32 has an end to cap the acetabular cup 2. In the preferred embodiment, the handle 31 is shaped with hand-hold style, and has a gasket 311 on other side connecting a head 422. Furthermore, the extension portion 32 has 4 fold angles with one side open and keeps an eccentric distance with respect to the axis of the acetabular cup 2. The end of extension portion 32 is equipped with a load-bearing head 321 for engaging the acetabular cup 2. In addition, the shell body 3 equipped with at least one bush 322 for fixing the drive rod 41 which would slide and swirl inside the extension portion 32. In other embodiment two bushes 322 may be utilized.

The drive shaft 4 partly assembled in the shell body 3 includes a drive rod 41 and a handle bar 42. In preferred embodiment, one end of the drive rod 41 and whole handle bar 42 are installed and extended out of the shell body 3.

The drive rod 41 has a connector 4112 near the end of the extension portion 32 to engage the acetabular cup 2 through the hole 21 and has a pivot 4151 at the other distal end to which a handle bar 42 is connected via the drive rod 41. In preferred embodiment, the shell body 3 has a bush 322 for housing the drive rod 41. Furthermore, the connector 4112 uses screw thread securing the acetabular cup 2, due to the female thread of the hole 21 mating the pin thread of connector 4112. The handle bar 42 with L-shape has one end connects to the pivot 4151 that one side of the end connecting to the pivot 4151 has a gasket 311 thereon. The cam 421 slides on the gasket 311. The drive rod 41 comprises at least five drive rods, the last drive rod has one end using a universal joint to connect the previous drive rod and another distal end connecting the pivot.

Wherein the head 422 has a guide hole 423 to house the handle bar 42 that controls the angular displacement of the pivot 4151 through the guide hole 423.

Furthermore, the drive rod 41 includes a first drive rod 411, a second drive 412, a third drive rod 413, a fourth drive rod 414 and a fifth drive rod 415. The second drive rod 412 uses a first universal joint 4111 to couple the first drive rod 411, which has a connector 4112 on the other distal end. Next, the third drive rod 413 uses a second universal joint 4121 to couple the second drive rod 412. Lastly, the fourth drive rod 414 uses a third universal joint 4131 to couple the third drive rod 413. Finally, the fifth drive rod 415 has one end using a fourth universal joint 4141 to couple the fourth drive rod 414 and other distal end connecting the pivot 4151.

Figure 4:
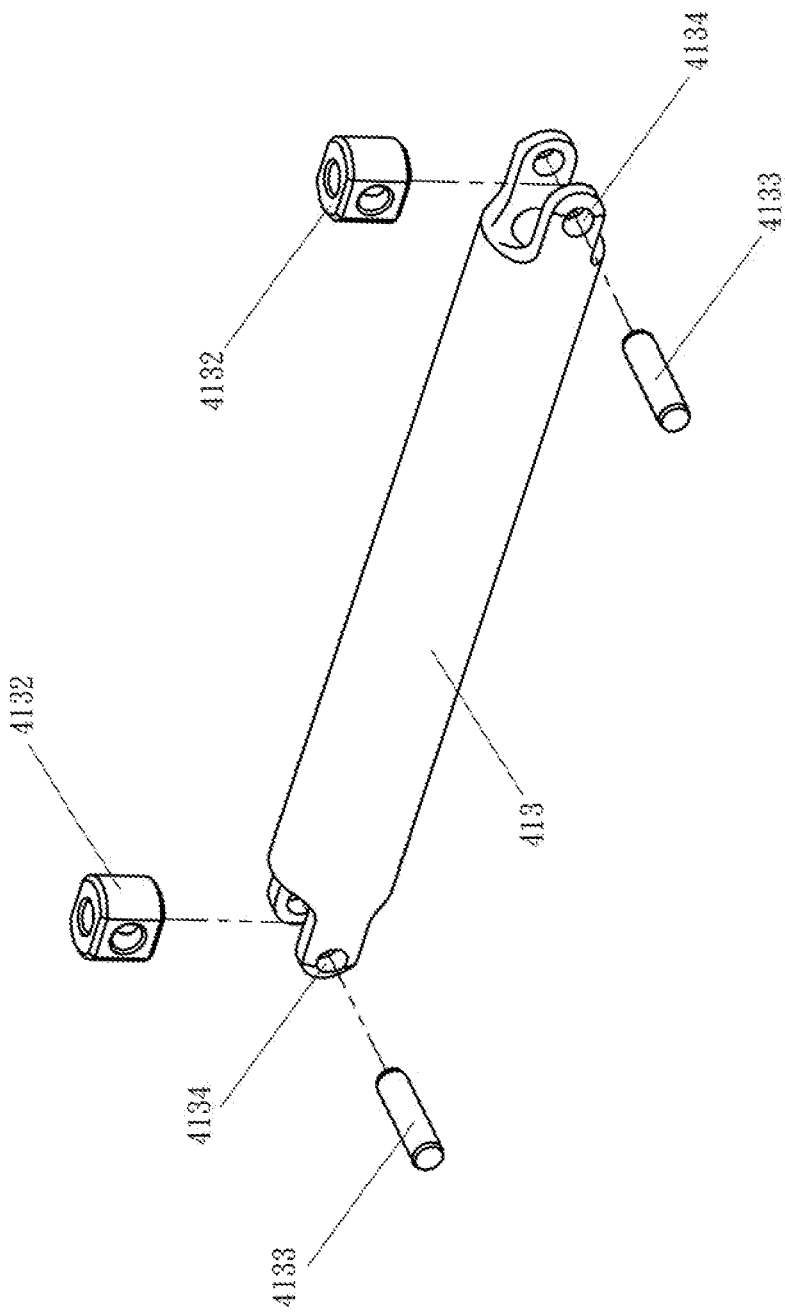
FIG. 4 is an assembled view of the drive rod and universal joint according to the present invention.

Referring FIG. 4, there is shown an assembled view of the drive rod and universal joint. The third drive rod 413 uses a second universal joint 4121 to connect the second drive rod 412, on the other distal end, it uses a third universal joint 4131 to connect the fourth drive rod 414. The universal joint mentioned includes a cross shaft 4132 and a hinge 4133 that both ends of the third drive rod 413 have through holes 4134 to join the hinge 4133 and the cross shaft 4132 in mechanism of universal joint. Those skilled in art would realize as the third rod 413 rotates, the second drive rod 412 with the first drive rod 411, and the fourth drive rod 414 with the fifth drive rod 415 rotate correspondingly.

The embodiment mention above describes an example for universal joint. Four universal joints 4111, 4121, 4131, 4141 joint the first drive rod 411, the second drive rod 412, the third drive rod 411, the fourth drive rod 414 and the fifth drive rod 415 to form the drive rod 41 using the same mechanism motioned above. The combination of these drive rods creates the axis that the shell body 3 should be aligned and impacted on.

Figure 5:
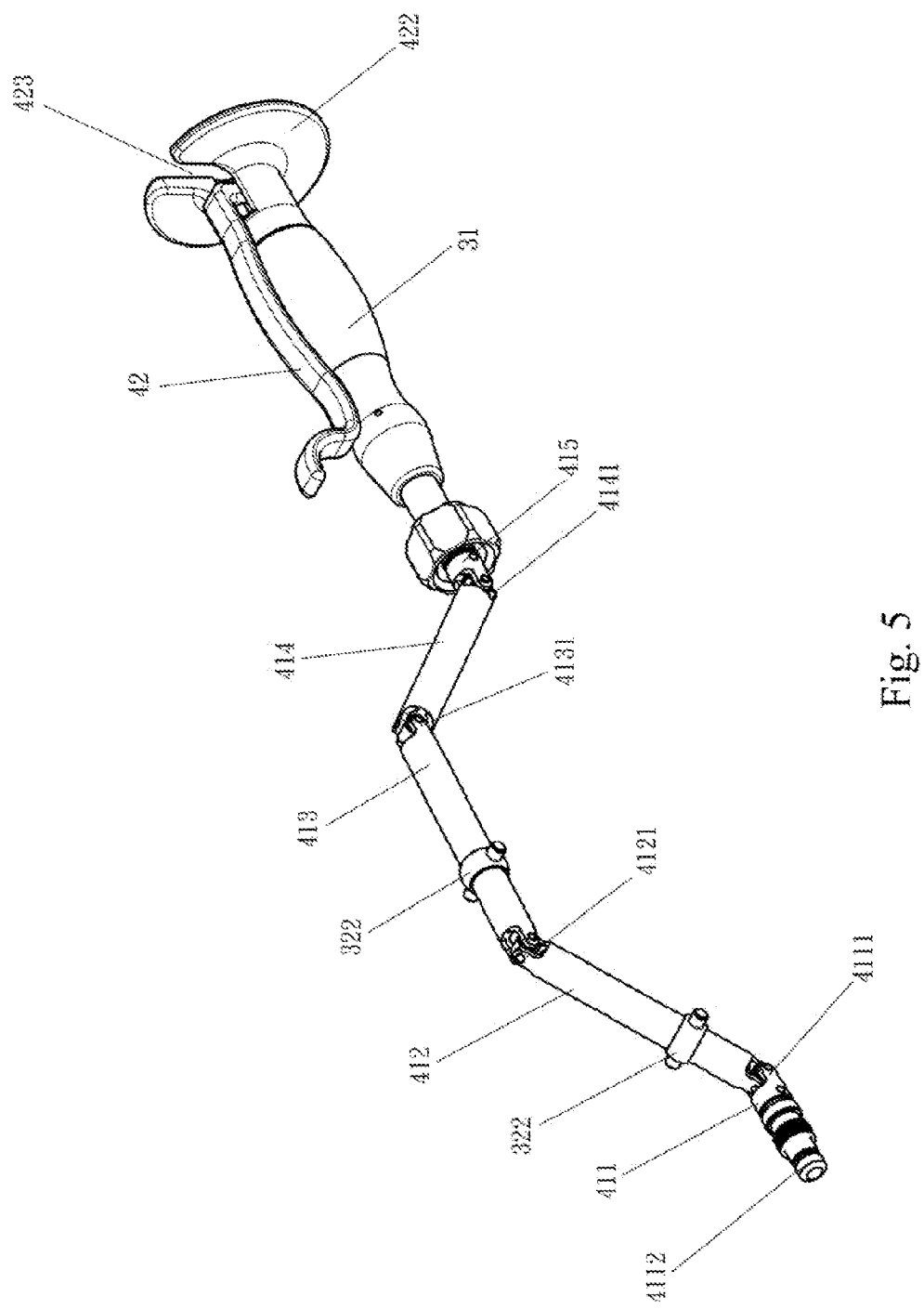
FIG. 5 is an isometric view of the drive shaft of the present invention.

Referring FIG. 5 there is shown an isometric view of the preferred embodiment of the present invention that the drive shaft 4 at least includes a drive rod 41, which is assembled with the first drive rod 411, the second drive rod 412, the third drive rod 413, the fourth drive rod 414 and the fifth drive rod 415 coupling each other one by one with four universal joints 4111, 4121, 4131, 4141.

Accordingly, the shell body 3 at least has a bush 322 for housing and holding the drive rod 41 in avoid of undesired shaking and moving. In the embodiment, there are two bushes 322 to stable the drive rod 41.

Furthermore, the bushes 322 are slid and swirled in the extension portion 32, thus restricting the movement of the drive rod 41 in the shell body 3. The bushes 322 can be placed at any two of the second drive rod 412, the third drive rod 413 or the fourth drive rod 414. The preferred embodiment in FIG. 5 shown two bushes 322 are set at the second drive rod 412 and the third drive rod 413.

Figure 6:
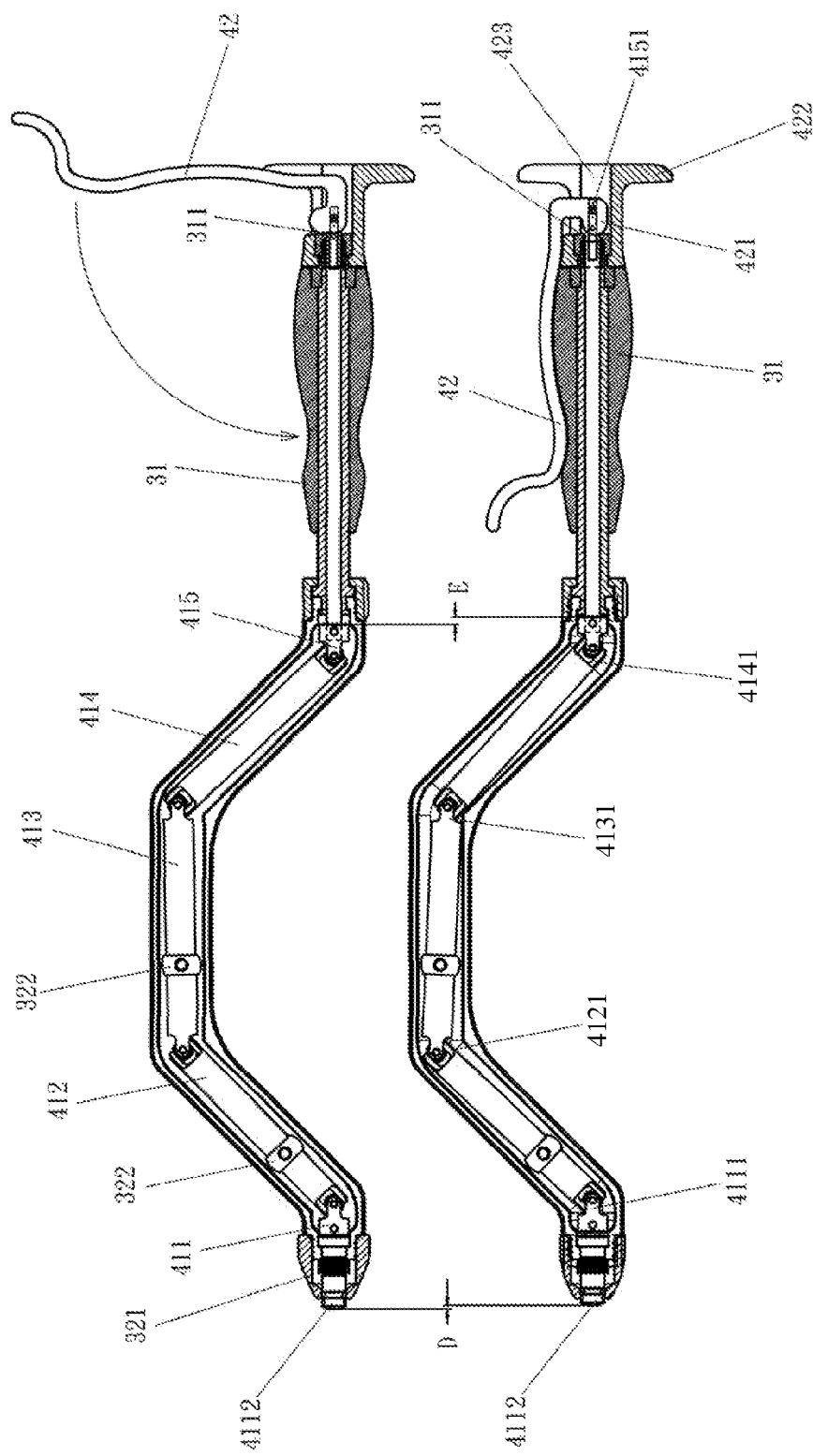
FIG. 6 is an isometric view of the second preferred embodiment of the present invention.

Referring FIG. 6 there is shown an isometric view of the second preferred embodiment of the present invention that the handle bar 42 engages the pivot 4151 for angular displacement having forward position and backward position. In the forward position the drive rod 41 rotates the acetabular cup 2 forward, and in the backward position the drive rod 41 shifts backward resulting in the acetabular cup 2 engaged the extension portion 32. The extension portion 32 has an end equipped with a load-bearing head 321 for engaging the acetabular cup 2.

From the mentioned above, the handle bar 42 shown in surgical instrument 1 has first place where an operator moves the handle bar 42 to the forward position causing the handle bar moves the drive rod forward. Next, the operator rotates the handle bar 42 to adjust the acetabular cup 2 in proper angle.

Correspondingly, after the acetabular cup 2 is in proper angle, the handle bar 42 has second place where an operator moves the handle bar 42 to the backward position. Then, the acetabular cup 2 is fixed and cannot rotate while the operator inserts the acetabular cup 2 in the position of acetabulum. After moving handle bar 42 to forward position again, the operator rotates it to release the acetabular cup 2. Thus, rotation of the handle bar 42 results in the gripping or releasing of the acetabular cup 2 or insert from surgical instrument 1.

Wherein the handle bar 42 has a gasket 311 on one side, and includes a cam 421 sliding on the gasket 311. In the forward position the handle bar 42 is pushed from position perpendicular to the handle bar 42 to the position horizontal with the handle bar 42 in backward position. Thus the cam 421 slides on the gasket 311 resulting in the drive rod 41 moving backward.

Figure 7:
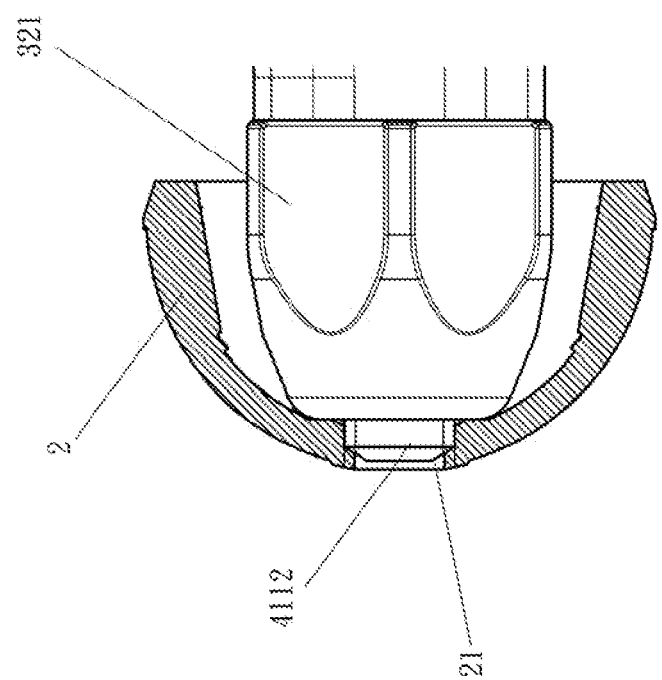
FIG. 7 is a sectional isometric view of the third preferred embodiment of the present invention.

Referring FIG. 7 there is shown a sectional isometric view of the third preferred embodiment of the present invention that the connector 4112 uses screw thread secures the acetabular cup 2. The hole 2 has female thread and the connector 4112 has pin thread. When the drive rod 41 moves backward, the connector 4112 is pull back until the load-bearing head 321 withstands and stops the acetabular cup 2. At that position, the pin thread of connector 4112 mating with female thread of hole 21 gripes acetabular cup 2.

Alternatively, the connector 4112 is pushed ahead when the drive rod 41 moves forward, and the acetabular cup 2 is separated from the load-bearing head 321. At that position, the connector 4112 with pin thread disconnects hole with female thread. Thus, movement of the drive rod 41 results in the gripping or releasing of the acetabular cup 2. As shown, the drive shaft 4 shifted at E distance as the handle bar 42 in the forward position is pushed from perpendicular position to the horizontal position. The E distance is transferred to connector 4112 causing a D distance backward.

Figure 8:
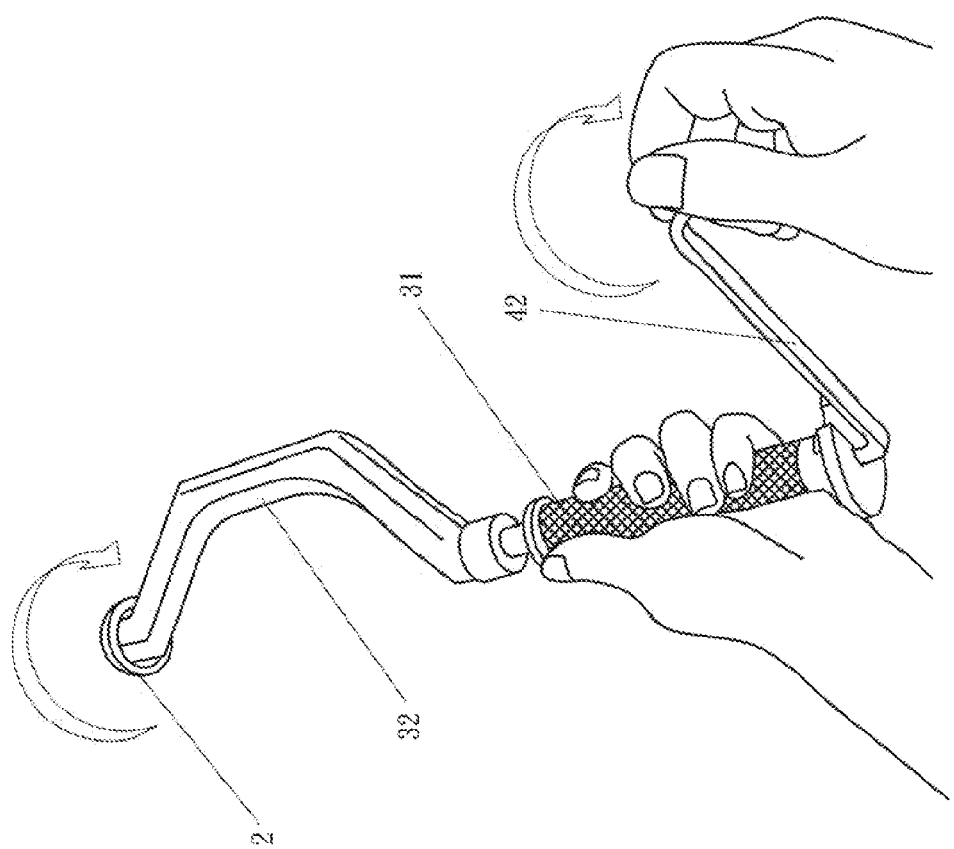
FIG. 8 is an isometric view of the fourth preferred embodiment of the present invention.

Referring FIG. 8 there is shown a sectional isometric view of the fourth preferred embodiment of the present invention that the surgical instrument for acetabular cup implantation 1 can be operated with only one hand holding the handle 31 and rotating the handle bar 42. The invention provides a handy implantation instrument for medical personnel to operate without difficulties. It promotes ergonomic operation concerning the total hip artificial joint.

From the above description, the operator rotates the handle bar to control the acetabular cup into the position. It is noted that the present invention has the advantages that the invention provides a clear and ergonomic instrument for medical personnel concerning the operation of acetabular cup implantation and making practical progress on the field.

While the invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A surgical instrument for acetabular cup implantation, which comprises:
   an acetabular cup having a hole thereon;
   a shell body having a handle and an extension portion, wherein the extension portion has an end to cap the acetabular cup; and
   a drive shaft being partly assembled in the shell body, comprising:
   a drive rod having a connector near the end of the extension portion to engage the hole and a pivot at another distal end; and
   a handle bar connecting to the pivot of the drive rod,
   wherein the handle bar with shifting angles drives the pivot forward and backward, in a forward position the handle bar moves the drive rod forward and is able to rotate the acetabular cup via the drive rod, and in a backward position the handle bar shifts the drive rod resulting in the acetabular cup being engaged to the end of extension portion; wherein the drive rod comprises:
   a first drive rod having the connector;
   a second drive rod using a first universal joint to connect the first drive rod;
   a third drive rod using a second universal joint to connect the second drive rod;
   a fourth drive rod using a third universal joint to connect the third drive rod; and
   a fifth drive rod having one end using a fourth universal joint to connect the fourth drive rod and another distal end connecting the pivot.

2. The surgical instrument for acetabular cup implantation as claimed in claim 1, wherein the extension portion has an end equipped with a load-bearing head for engaging the acetabular cup.

3. The surgical instrument for acetabular cup implantation as claimed in claim 1, wherein the connector uses screw thread to secure the acetabular cup.

4. The surgical instrument for acetabular cup implantation as claimed in claim 3, wherein the hole has female thread defined on an inner surface and the connector has pin thread defined on an outer surface.

5. The surgical instrument for acetabular cup implantation as claimed in claim 1, wherein the shell body at least has a bush for housing the drive rod.

6. The surgical instrument for acetabular cup implantation as claimed in claim 1, wherein the drive rod comprises at least five drive rods, a last drive rod has one end using a universal joint to connect a previous drive rod and another distal end connecting the pivot.

7. The surgical instrument for acetabular cup implantation as claimed in claim 1, wherein the handle has an end connecting a head.

8. The surgical instrument for acetabular cup implantation as claimed in claim 7, wherein the head has a guide hole to house the handle bar.

9. The surgical instrument for acetabular cup implantation as claimed in claim 1, wherein the handle has a gasket on one side, and the handle bar comprises a cam sliding on the gasket.

* * * * *